(12) United States Patent
Chu et al.

(10) Patent No.: US 8,597,674 B2
(45) Date of Patent: *Dec. 3, 2013

(54) IN SITU BLOOD VESSEL AND ANEURYSM TREATMENT

(75) Inventors: Jack Chu, Santa Rosa, CA (US); Brian Raze, Windsor, CA (US)

(73) Assignee: Medtronic Vascular, Inc., Santa Rosa, CA (US)

(*) Notice: Subject to any disclaimer, the term of this patent is extended or adjusted under 35 U.S.C. 154(b) by 743 days.

This patent is subject to a terminal disclaimer.

(21) Appl. No.: 12/132,355

(22) Filed: Jun. 3, 2008

(65) Prior Publication Data

US 2008/0249511 A1 Oct. 9, 2008

Related U.S. Application Data

(63) Continuation of application No. 10/424,005, filed on Apr. 25, 2003, now Pat. No. 7,396,540.

(51) Int. Cl.
*A61F 2/00* (2006.01)
*A61F 2/06* (2013.01)
*A61M 29/00* (2006.01)

(52) U.S. Cl.
USPC .......................... 424/423; 623/1.1; 606/195

(58) Field of Classification Search
USPC ............... 604/96.01, 164.01, 523, 507, 508; 424/423; 623/1.1; 606/195
See application file for complete search history.

(56) References Cited

U.S. PATENT DOCUMENTS

| | | | |
|---|---|---|---|
| 4,638,803 A | 1/1987 | Rand | |
| 5,213,580 A * | 5/1993 | Slepian et al. | 128/898 |
| 5,527,355 A | 6/1996 | Ahn | |
| 5,538,504 A | 7/1996 | Linden et al. | |
| 5,670,161 A | 9/1997 | Healy et al. | |
| 5,713,917 A | 2/1998 | Leonhardt et al. | |
| 5,741,283 A | 4/1998 | Fahy | |
| 5,824,054 A | 10/1998 | Khosravi et al. | |
| 5,916,235 A | 6/1999 | Guglielmi | |
| 6,139,520 A | 10/2000 | McCrory et al. | |

(Continued)

FOREIGN PATENT DOCUMENTS

WO    WO02/15824    2/2002

OTHER PUBLICATIONS

Chaikof, Elliot L. "Biomaterials and Scaffolds in Reparative Medicine" Ann. N.Y. Acad. Sci. 961:96-105(2002) New York Academy of Sciences, New York.

(Continued)

*Primary Examiner* — Kevin C Sirmons
*Assistant Examiner* — Imani Hayman

(57) ABSTRACT

Treatment of aneurysmal blood vessels with local delivery of therapeutic agents thereby reduces or lessens the severity of an aneurysm, and, where used in conjunction with the placement of an excluding device, provides for more rapid recovery of the blood vessel from any disturbance occurring during placement of the excluding device. Therapeutic agents are placed in the aneurysmal site in a time-release carrier medium, such that the therapeutic agent is released into the aneurysmal site over a period of time without the need to provide systemic introduction of the therapeutic agent. The carrier may be introduced through the patient's dermis, such as with the use of a laparoscope, or intravascularly, through the use of a catheter. The carrier may be in a solid matrix, viscous liquid or liquid form.

15 Claims, 12 Drawing Sheets

(56) References Cited

U.S. PATENT DOCUMENTS

| | | | |
|---|---|---|---|
| 6,159,239 | A | 12/2000 | Greenhalgh |
| 6,190,353 | B1 | 2/2001 | Makower et al. |
| 6,302,870 | B1 | 10/2001 | Jacobsen et al. |
| 6,335,384 | B1 | 1/2002 | Evans et al. |
| 6,344,035 | B1 | 2/2002 | Chudzik et al. |
| 6,348,050 | B1 | 2/2002 | Hartlaub |
| 6,364,823 | B1 | 4/2002 | Garibaldi et al. |
| 6,364,903 | B2 | 4/2002 | Tseng et al. |
| 6,368,346 | B1 | 4/2002 | Jadhav |
| 6,371,970 | B1 | 4/2002 | Khosravi et al. |
| 6,376,742 | B1 | 4/2002 | Zdrahala et al. |
| 6,379,329 | B1 | 4/2002 | Naglreiter et al. |
| 6,387,121 | B1 | 5/2002 | Alt |
| 6,451,373 | B1 | 9/2002 | Hossainy et al. |
| 6,475,466 | B1 | 11/2002 | Ricci et al. |
| 6,506,410 | B1 | 1/2003 | Park et al. |
| 6,531,154 | B1 | 3/2003 | Mathiowitz et al. |
| 6,541,515 | B2 | 4/2003 | Singh et al. |
| 6,676,971 | B2 * | 1/2004 | Goupil et al. ............... 424/489 |
| 6,855,153 | B2 | 2/2005 | Saadat |
| 7,371,228 | B2 | 5/2008 | Chu et al. |
| 2002/0065546 | A1 | 5/2002 | Machan et al. |
| 2002/0160034 | A1 | 10/2002 | Levesque et al. |
| 2003/0014075 | A1 | 1/2003 | Rosenbluth et al. |
| 2003/0018294 | A1 | 1/2003 | Cox |
| 2003/0100942 | A1 | 5/2003 | Ken et al. |
| 2004/0199241 | A1 | 10/2004 | Gravett et al. |
| 2004/0215334 | A1 | 10/2004 | Fernandes et al. |
| 2005/0004660 | A1 | 1/2005 | Rosenbluth et al. |
| 2005/0266043 | A1 | 12/2005 | Tseng et al. |

OTHER PUBLICATIONS

Griffith, Linda G. "Emerging Design Principles in Biomaterials and Scaffolds for Tissue Engineering" Ann. N.Y. Acad. Sci 961: 83-95 (2002). New York Academy of Sciences, New York.

Ochoa, Erin R. et al. "An Overview of the Pathology and Approaches to Tissue Engineering" Annals New York Academy of Sciences. 2002, 979: 10-26.

Goodman, Louis Sanford and Albert Gilman. The Pharmacological Basisi of Therapeutics. New York:McGraw-Hill, 2001.

* cited by examiner

IN SITU BLOOD VESSEL AND ANEURYSM TREATMENT

CROSS REFERENCE TO RELATED APPLICATIONS

The present application is a continuation of co-pending U.S. patent application Ser. No. 10/424,005 filed Apr. 25, 2003 and incorporated herein in its entirety.

BACKGROUND OF THE INVENTION

1. Field of the Invention

Embodiments of the present invention generally relate to the field of the treatment of body lumens, more particularly to the field of the treatment of blood vessels, and more particularly to the treatment of blood vessel aneurysms with stents, lined stents such as stent grafts, and the use of pharmaceutical agents therewith for the treatment of localized blood vessel phenomena, such as aneurysm.

2. Description of the Related Art

Aneurysm, i.e., the enlargement of a blood vessel at a specific location therein to the point where rupture of the blood vessel is imminent, has been treated in the past by surgical intervention techniques, whereby the affected portion of the blood vessel is removed and is replaced by a synthetic graft. This treatment regimen is highly invasive for the patient, and typically requires a multiple day post-operative hospital stay, as well as several months of recovery time until the patient has fully recovered from the surgery. Additionally, some patients may not capable of undergoing such a procedure due to morbidity or other overall health issues.

To address the limitations imposed by surgical intervention to replace the aneurysmal blood vessel region with an artificial graft, a new technique has been developed by which the aneurysmal blood vessel site is treated by placing a lined stent, known in the art as a stent graft, within the blood vessel in a position by which the tubular body of the stent graft spans the interior of the weakened area of the blood vessel wall. The stent graft, properly positioned, will allow blood to flow through the hollow tubular interior thereof, and also prevent blood, under systemic pressure, from reaching the weakened blood vessel wall at the aneurysmal site spanned by the tubular body thereof. However, there is still the opportunity for blood to reach the weakened wall location, such as through leakage of blood between the stent and the vessel wall and thus into the weakened region, diffusion of blood through the stent material itself, or re-supply of blood into the aneurysmal sac from adjacent blood vessels. In each case, there is a renewed risk that the blood vessel may rupture. Furthermore, there remains a risk of additional deterioration of the blood vessel wall at the aneurysmal location even in the absence of blood leakage into the region isolated by the stent graft or the renewed supply of blood to the isolated region.

Typically, surgical intervention for aneurysm repair is not indicated until the blood vessel diameter, at the aneurysmal site, is at least 150 to 300% of its normal diameter. Below this threshold, the normal course of treatment has been to monitor the site, and if the diameter of the blood vessel wall at the aneurysmal site continues to expand beyond an undesirable threshold diameter, intervene surgically. Recently, it has been found that the application of certain antibiotics and other aneurysmal attack inhibitors, can reduce the severity and/or progression of an aneurysm, and thereby reduce the likelihood of the need for surgical intervention to repair the aneurysm. It is postulated that the antibiotic or other inhibitor reduces the level of an elastin or collagen attacking protein in the bloodstream and blood vessel wall, specifically matrix metalloproteinasis, MMP2 and MMP9. This reduces the severity of an attack based on MMP2 and MMP9 and other MMPs on the elastin cells in the blood vessel wall and thus reduces the severity and the progression of the aneurysm. Antibiotics such as doxycycline, as well as beta adregenic blockage agents, ACE inhibitors, anti-inflammation drugs have been found to suppress aneurysm progression.

Typical antibiotic or other based treatment requires the use of systemic antibiotics, either orally, intramuscularly or intravenously introduced, in a dosage sufficient to ensure that the quantity of antibiotic reaching the aneurysm is sufficient to affect the elastin, collagen attacking protein level at the aneurysm site. Thus, far more antibiotic must be used than that needed to treat the aneurysm, because a substantial portion of the antibiotic is directed to locations other than the aneurysmal site. The systemic use of antibiotics to treat localized sites can lead to serious side effects, including the occurrence of drug resistant bacteria, gastrointestinal disruption, and the like. The longer the duration of time that antibiotics are taken, and the higher the dosage, the higher the risk of such serious side effects.

One additional proposed mechanism for treating blood vessels which are in an aneurysmal state, but for which surgery is not yet indicated, is to introduce "micro-spheres" containing a quantity of a therapeutic agent, into the sac space between the sac wall and the stent graft. Such microspheres are constructed to provide a time release of the pharmaceutical agent, and thus provide long term dosing of the aneurysmal site. These microspheres are typically configured to have a diameter on the order of 50 microns or more, such that sufficient therapeutic agent can be carried therein to enable a relatively long-term release of the therapeutic agent from the microsphere into the bloodstream. Because, microspheres of this size can cause substantial complications, such as the blockage of smaller capillaries or distal thrombosis; they are not recommended to be introduced in the blood stream. Additionally, only a small portion of the therapeutic agent released from the microspheres actually reaches the aneurysm, because the majority of the agent becomes distributed throughout the body by the patient's blood. Therefore, although the microspheres provide the patient with longer term regular dosing of the therapeutic agent, and thus free the patient from the need to regularly ingest or inject the agent, they do not provide long term localized delivery of therapeutic agents directly to the aneurismal site.

Therefore, there exists a need in the art for a localized drug delivery system, which will allow timed delivery of therapeutic agents to an aneurysmal site in a blood vessel, after placement of a bypassing element or prosthesis, such as placing a stent graft in the blood vessel to span the aneurysmal site, without the need for systemic application of the therapeutic agent.

SUMMARY OF THE INVENTION

The present invention provides methods and apparatus for the treatment of blood vessels with therapeutic agents, with localized application of a therapeutic agent in a localized treatment site.

In one aspect, the invention includes a carrier, configured to be received in a blood vessel and retained therein in a desired location, such carrier including a therapeutic agent therewith which is released over a period of time. The carrier may be a matrix material, having the therapeutic agent received therein for delivery, over time, to the desired location in the blood vessel. The carrier may be affixed to the blood vessel wall, at or adjacent the aneurysmal site, thereby enabling delivery of the therapeutic agent directly from the carrier to the wall of the aneurysmal site.

In a further aspect, the carrier is located at the aneurysmal site, and held in that position such that an excluding device, such as a stent graft, may be located to span the aneurysmal site and trap the carrier in a position between the aneurysmal site and the excluding device, such that the carrier need not be attached to the blood vessel wall to enable maintenance of the carrier at the aneurysmal site. The carrier may be positioned, such that the excluding device is physically positioned in contact with both the excluding device and the aneurysmal blood vessel wall. Alternatively, the carrier may be simply maintained in the aneurysmal sac, such that the carrier need not be, but may be, in contact with the aneurysmal blood vessel wall.

The carrier may be positioned in the aneurysmal blood vessel by introduction thereof via a blood vessel, such as a leg blood vessel, and carried to the aneurysmal site via a catheter or a wire, and attached to the aneurysmal blood vessel at the aneurysmal site, such as with a mechanical attachment device or an adhesive, or may be directly injected into the blood vessel wall at the aneurismal site. Additionally, the carrier may be positioned in the blood vessel at the aneurysmal site and held in place by the placement device, such as a catheter or wire, as an exclusion device is located to span or bypass the aneurysmal site. Additionally, the carrier may be placed in the aneurysmal sac after the exclusion device is located to span the aneurysmal location, such as by placement thereof by catheter or wire through a blood vessel and then between the blood vessel wall and the excluding device, or, by introduction through the body, such as by needle aspiration and then injection of the carrier through the puncture in the blood vessel wall created by the needle, and into the aneurysmal sac between the aneurysmal blood vessel wall and the excluding device.

BRIEF DESCRIPTION OF THE DRAWINGS

So that the manner in which the above recited features of the present invention can be understood in detail, a more particular description according to features briefly summarized above, may be had by reference to embodiments, some of which are illustrated in the appended drawings. It is to be noted, that the appended drawings illustrate only typical embodiments of this invention and are therefore not to be considered limiting of its scope, for the invention may admit to other equally effective embodiments.

DETAILED DESCRIPTION OF THE INVENTION

Figure 1:
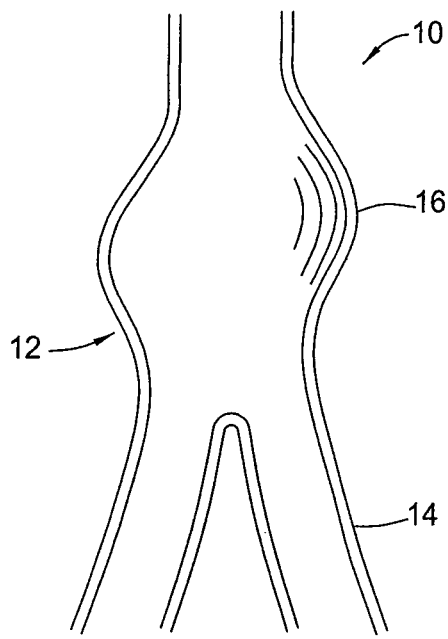
FIG. 1 is a schematic view of a human aneurysmal blood vessel, specifically an aorta, showing an aneurysmal site therein.

Referring initially to FIG. 1, there is shown an aneurysmal blood vessel 10, in particular, there is shown an aorta 12 undergoing an aneurysmal event, such that the aorta or blood vessel wall 14 is enlarged at an aneurysmal site 16 and the diameter of the aorta 12 at the aneurysmal site 16 is on the order of over 150% to 300% of the diameter of a healthy aorta 12, or a diameter of five cm or greater. The aneurysmal site 16 forms an aneurysmal bulge or sac 18. If left untreated, the aneurysmal sac 18 may continue to deteriorate, increase in size, and eventually tear or burst.

Non-surgical intervention to treat aneurysm is a recent development, and, as previously discussed herein, involves the use of systemic therapeutic agents, such as antibiotics (such as doxycycline) or other MMP2 and MMP9 or other MMPs inhibitors to reduce the attack on the blood vessel elastin or collagen at the aneurysmal site 16. It is believed that by reducing the incidence of these MMP2 and MMP9 proteins, the aneurysmal site 16 will not progress and thus continue to expand and weaken, and in fact may heal of its own accord. However, such prior art techniques are problematic, in that they produce unwanted and undesirable side effects.

The present invention provides treatment of aneurysmal blood vessels, such as aorta 12, without the need for systemic therapy. Generally, the invention provides mechanism for sustained, time release of therapeutic agents at the local aneurysmal site, thereby enabling greater control of dosage to the aneurysmal site 16, as well as eliminating the problems associated with systemic therapy treatment. The therapeutic agents are disposed within a carrier 20 (see, e.g., FIG. 2), and are released thereby through eluting, diffusing or other release mechanisms. The carrier may be in a solid, gel or liquid form, and may be located both within and outside of the blood vessel at the aneurysmal site 16.

A carrier material provided is adapted to exhibit a combination of physical characteristics such as biocompatibility, and, preferably, biodegradability and bioabsorbability, while providing a delivery vehicle for release of one or more therapeutic agents that aid in the treatment of aneurysmal tissue. The carrier material used is biocompatible such that it results in no induction of inflammation or irritation when implanted, degraded or absorbed.

Thus, the carrier according to the present invention may be either biodegradable or non-biodegradable. Representative examples of biodegradable compositions include albumin, collagen, gelatin, hyaluronic acid, starch, cellulose and cellulose derivatives (e.g., methylcellulose, hydroxypropylcellulose, hydroxypropyl-methylcellulose, carboxymethylcellulose, cellulose acetate phthalate, cellulose acetate succinate, hydroxypropylmethylcellulose phthalate), casein, dextran, polysaccharides, fibrinogen, poly(D,L-lactide), poly (D,L-lactide-co-glycolide), poly(glycolide), poly(hydroxybutyrate), poly(alkylcarbonate) and poly(orthoesters), polyesters, poly(hydroxyvaleric acid), polydioxanone, poly (ethylene terephthalate), poly(malic acid), poly(tartronic acid), polyanhydrides, polyphosphazenes, poly(amino acids) and their copolymers.

Representative examples of non-degradable polymers include poly(ethylene-vinyl acetate) ("EVA") copolymers, silicone rubber, acrylic polymers (polyacrylic acid, polymethylacrylic acid, polymethylmethacrylate, polyalkylcynoacrylate), polyethylene, polypropylene, polyamides (nylon 6,6), polyurethane, poly(ester urethanes), poly(ether urethanes), poly(ester-urea), polyethers (poly(ethylene oxide), poly(propylene oxide), pluronics and poly(tetramethylene glycol)), silicone rubbers and vinyl polymers (polyvinylpyrrolidone, poly(vinyl alcohol), poly(vinyl acetate phthalate). Polymers also may be developed which are either anionic (e.g., alginate, carboxymethyl cellulose and poly(acrylic acid), or cationic (e.g., chitosan, poly-L-lysine, polyethylenimine, and poly(allyl amine)).

Preferred polymeric carriers include poly(ethylene-vinyl acetate), polyurethanes, poly(D,L-lactic acid) oligomers and polymers, poly(L-lactic acid) oligomers and polymers, poly (glycolic acid), copolymers of lactic acid and glycolic acid, poly (caprolactone), poly (valerolactone), polyanhydrides, copolymers of poly (caprolactone) or poly (lactic acid) with a polyethylene glycol (e.g., MePEG), and blends, admixtures, or co-polymers of any of the above. Other preferred polymers include polysaccharides such as hyaluronic acid, chitosan and fucans, and copolymers of polysaccharides with degradable polymers.

Other polymers useful for these applications include carboxylic polymers, polyacetates, polyacrylamides, polycarbonates, polyethers, polyesters, polyethylenes, polyvinylbutyrals, polysilanes, polyureas, polyurethanes, polyoxides, polystyrenes, polysulfides, polysulfones, polysulfonides, polyvinylhalides, pyrrolidones, thermal-setting polymers, cross-linkable acrylic and methacrylic polymers, ethylene acrylic acid copolymers, styrene acrylic copolymers, vinyl acetate polymers and copolymers, vinyl acetal polymers and copolymers, epoxy, melamine, other amino resins, phenolic polymers, and copolymers thereof, water-insoluble cellulose ester polymers (including cellulose acetate propionate, cellulose acetate, cellulose acetate butyrate, cellulose nitrate, cellulose acetate phthalate, and mixtures thereof), polyvinylpyrrolidone, polyethylene glycols, polyethylene oxide, polyvinyl alcohol, polyethers, polysaccharides, hydrophilic polyurethane, polyhydroxyacrylate, dextran, xanthan, hydroxypropyl cellulose, methyl cellulose, and homopolymers and copolymers of N-vinylpyrrolidone, N-vinyllactam, N-vinyl butyrolactam, N-vinyl caprolactam, other vinyl compounds having polar pendant groups, acrylate and methacrylate having hydrophilic esterifying groups, hydroxyacrylate, and acrylic acid, and combinations thereof, cellulose esters and ethers, ethyl cellulose, hydroxyethyl cellulose, cellulose nitrate, cellulose acetate, cellulose acetate butyrate, cellulose acetate propionate, polyurethane, polyacrylate, natural and synthetic elastomers, rubber, acetal, nylon, polyester, styrene polybutadiene, acrylic resin, polyvinylidene chloride, polycarbonate, homopolymers and copolymers of vinyl compounds, polyvinylchloride, polyvinylchloride acetate. In general, see U.S. Pat. No. 6,514,515 to Williams; U.S. Pat. No. 6,506,410 to Park, et al.; U.S. Pat. No. 6,531,154 to Mathiowitz, et al.; U.S. Pat. No. 6,344,035 to Chudzik, et al.; U.S. Pat. No. 6,376,742 to Zdrahala, et al.; and Griffith, L. A., Ann. N.Y. Acad. of Sciences, 961:83-95 (2002); and Chaikof, et al, Ann. N.Y. Acad. of Sciences, 961:96-105 (2002).

Additionally, polymers as described herein can also be blended or copolymerized in various compositions as required.

The polymeric carriers as discussed can be fashioned in a variety of forms with desired release characteristics and/or with specific desired properties. For example, the polymeric coatings may be fashioned to release the therapeutic agent or agents upon exposure to a specific triggering event such as pH. Representative examples of pH-sensitive polymers include poly(acrylic acid) and its derivatives (including for example, homopolymers such as poly(aminocarboxylic acid); poly(acrylic acid); poly(methyl acrylic acid), copolymers of such homopolymers, and copolymers of poly(acrylic acid) and acrylmonomers such as those discussed above. Other pH sensitive polymers include polysaccharides such as cellulose acetate phthalate; hydroxypropylmethylcellulose phthalate; hydroxypropyl methylcellulose acetate succinate; cellulose acetate trimellilate; and chitosan. Yet other pH sensitive polymers include any mixture of a pH sensitive polymer and a water-soluble polymer.

Likewise, polymeric carriers can be fashioned that are temperature sensitive. Representative examples of thermogelling polymers and their gelatin temperature include homopolymers such as poly(N-methyl-N-n-propylacrylamide) (19.8° C.); poly(N-n-propylacrylamide) (21.5° C.); poly(N-methyl-N-isopropylacrylamide) (22.3° C.); poly(N-n-propylmethacrylamide) (28.0° C.); poly(N-isopropylacrylamide) (30.9° C.); poly(N,n-diethylacrylamide) (32.0° C.); poly(N-isopropylmethacrylamide) (44.0° C.); poly(N-cyclopropylacryl-amide) (45.5° C.); poly(N-ethylmethyacrylamide) (50.0° C.); poly(N-methyl-N-ethylacrylamide) (56.0° C.); poly(N-cyclopropylmethacrylamide) (59.0° C.); poly(N-ethylacrylamide) (72.0° C. C.). Moreover, thermogelling polymers may be made by preparing copolymers between (among) monomers of the above, or by combining such homopolymers with other water-soluble polymers such as acrylmonomers (e.g., acrylic acid and derivatives thereof such as methylacrylic acid, acrylate and derivatives thereof such as butyl methacrylate, acrylamide, and N-n-butyl acrylamide).

Other representative examples of thermogelling polymers include cellulose ether derivatives such as hydroxypropyl cellulose (41° C.); methyl cellulose (55° C.); hydroxypropylmethyl cellulose (66° C.); and ethylhydroxyethyl cellulose, and Pluronics such as F-127 (10-15° C.); L-122 (19° C.); L-92 (26° C.); L-81 (20° C.); and L-61 (24° C.).

The polymer used may be obtained from various chemical companies known to those with skill in the art. However, because of the presence of unreacted monomers, low molecular weight oligomers, catalysts, and other impurities, it may be desirable (and, depending upon the materials used, may be necessary) to increase the purity of the polymer used. The purification process yields polymers of better-known, purer composition, and therefore increases both the predictability and performance of the mechanical characteristics of the coatings. The purification process will depend on the polymer or polymers chosen. Generally, in the purification process, the polymer is dissolved in a suitable solvent. Suitable solvents include (but are not limited to) methylene chloride, ethyl acetate, chloroform, and tetrahydrofuran. The polymer solution usually is then mixed with a second material that is miscible with the solvent, but in which the polymer is not soluble, so that the polymer (but not appreciable quantities of impurities or unreacted monomer) precipitates out of solution. For example, a methylene chloride solution of the polymer may be mixed with heptane, causing the polymer to fall out of solution. The solvent mixture then is removed from the copolymer precipitate using conventional techniques. For information regarding stents and coatings, see U.S. Pat. No. 6,387,121 to Alt; U.S. Pat. No. 6,451,373 to Hossainy, et al.; and U.S. Pat. No. 6,364,903 to Tseng, et al.

Liquid or Gel Based Carriers and their Placement

Figure 2:
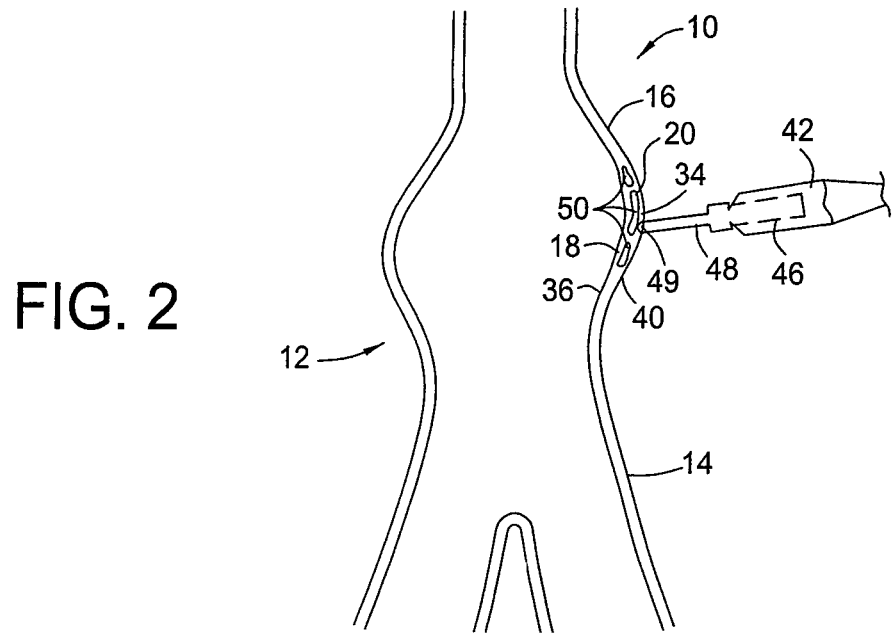
FIG. 2 is a sectional view of the aorta shown in FIG. 1, showing an intervention device therein for therapeutic treatment of the aneurysmal site.

Referring to FIG. 2, there is shown an embodiment of the invention, wherein the carrier 20 is of a gel or liquid form, and is located within the aorta wall 14. Specifically, in this embodiment, the carrier 20 is a liquid based carrier medium, preferably a gel such as a low viscosity sol gel or liposome type gel, in which the therapeutic agent is trapped for time release therefrom. This gel-based carrier is injected into the aorta wall 14 and maintained therein to dispense or elute, over time, the therapeutic agent. Preferably, the carrier 20 is placed by injection into the Tunica Media 34, which forms the muscular layer of the blood vessel wall 14 intermediate of the Tunica Intima 36, the inner surface 38 of which is in intimate contact with blood flowing through the aorta or other blood vessel, and the Tunica Adventitia 40, which forms the outer surface of aorta 12 or other blood vessel. By locating the carrier 20 within the Tunica Media 34, within which the elastin cells which provide elasticity and strength to the blood vessel wall 14 are located, the therapeutic agent in the gel is in intimate contact with the cells of greatest interest in aneurysm treatment, and thus should have the greatest possible efficacy in treatment of the underlying cause of the aneurysm.

In this embodiment, the material-forming carrier 20 preferably may be collagen, biodegradable polymer, fibrin, glue, a type of monodisperse hydrogel or sol gel, formed as a viscous slurry of nanoparticles. The nanoparticles are synthesized from poly-N-isopropylacrylamide (pNIPAm) lightly cross-linked with N,N-methylenebis(acrylamide) (BIS). The therapeutic agent is included during synthesis, and becomes trapped in the resulting material. After precipitation polymerization in aqueous media, the particles are centrifuged from the surrounding water, resulting in a relatively high viscosity gelatinous material. The viscosity may be modified by the addition of water, to lower the viscosity to enable delivery of the sol gel in a liquid form such as through a needle.

Figure 3:
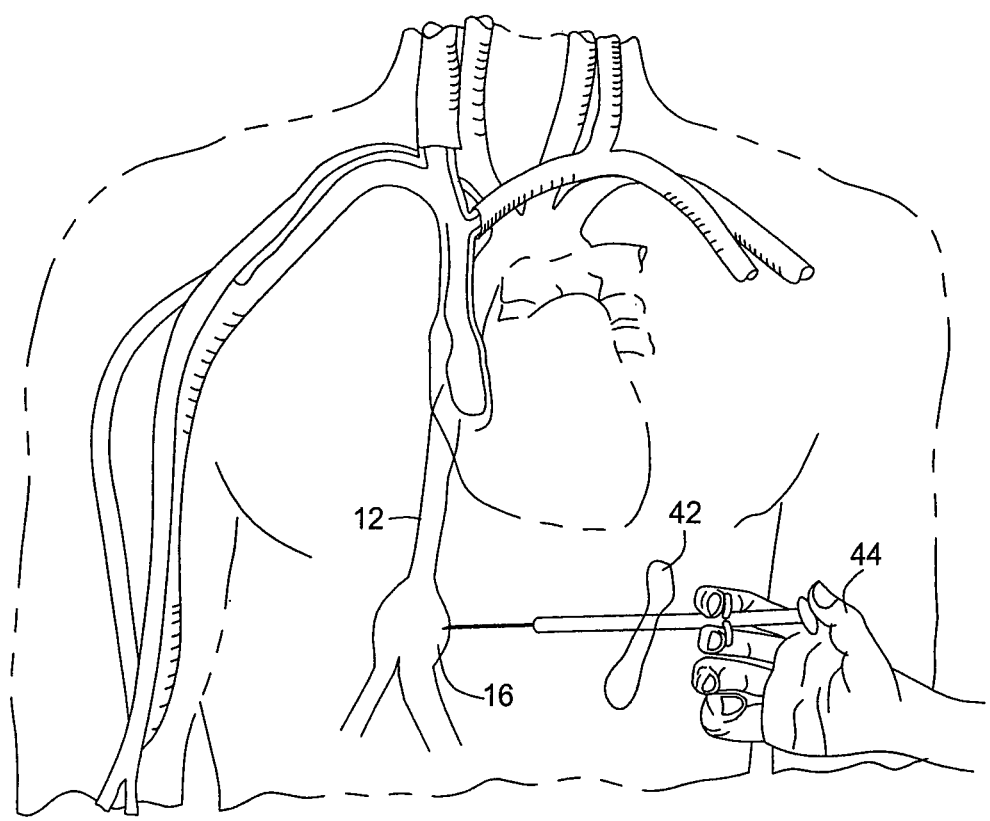
FIG. 3 is a view of the delivery mechanism for locating the intervention device of FIG. 3 in place for therapeutic treatment of the aneurysmal site.
Figure 5:
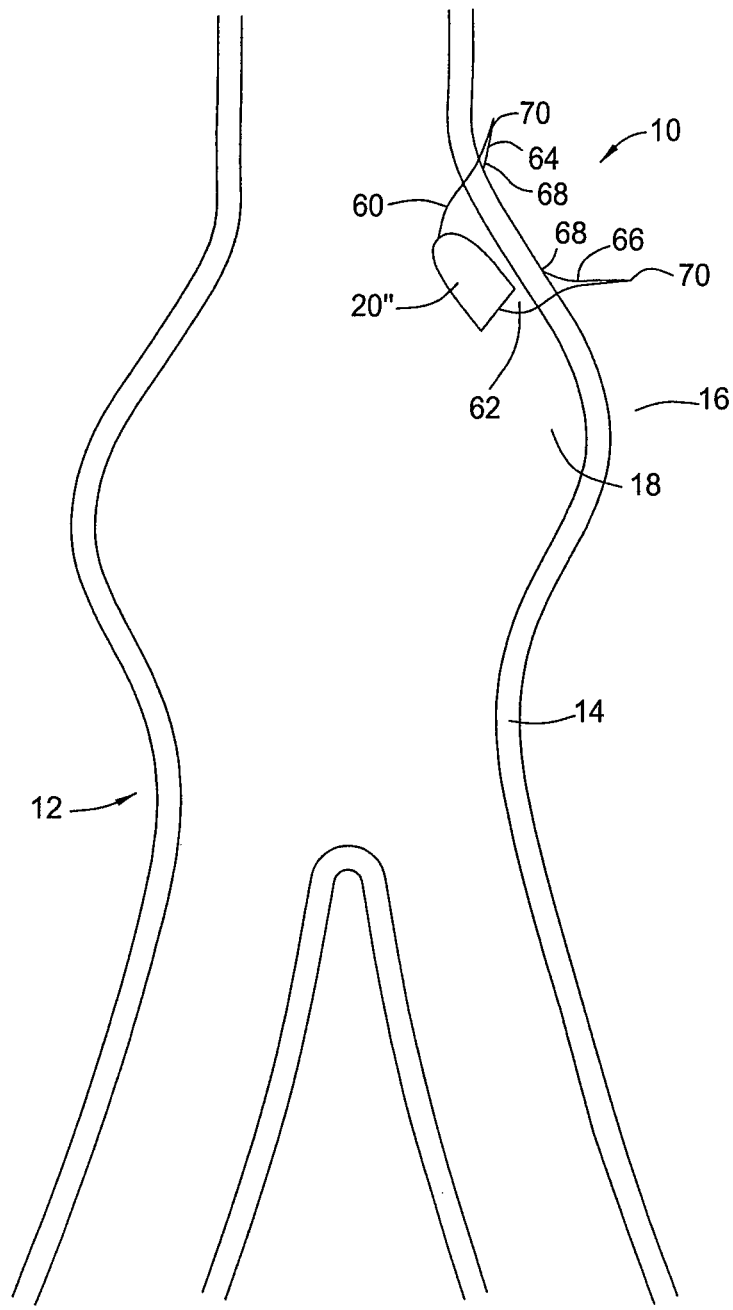
FIG. 5 is a sectional view of the aorta shown in FIG. 1, showing an additional intervention device therein for therapeutic treatment of the aneurysmal site.

Referring now to FIGS. 2 and 3, a mechanism for locating the carrier 20 and therapeutic agent therein in the Tunica Media is generically shown. A laparoscope 42 is operated by the hand 44 of a practitioner, to position a syringe 46 having the carrier 20 in gel form therein, in the proximity of an aneurysmal blood vessel wall 14 location. The syringe 46 includes a needle 49 thereon, which is configured to be manipulated into the region of the blood vessel wall 14 between the Tunica Intima 36 and Tunica Adventitia 40 as shown in FIG. 5. Once the needle is so located, a quantity of carrier 20 is injected, through an aperture 48 at the end of the needle 48, into the Tunica Media 34. Preferably, the needle 49 is manipulated, by the practitioner, to multiple localized sites on the aorta wall 14, such that carrier 20 may be located and maintained in multiple locations or sites 50 within the Tunica Media. After a sufficient, as determined by the practitioner or physician, quantity of the carrier is so positioned, the needle 48 and then the laparoscope are removed and the incision through which the laparoscope 42 was positioned is sutured shut.

Figure 13:
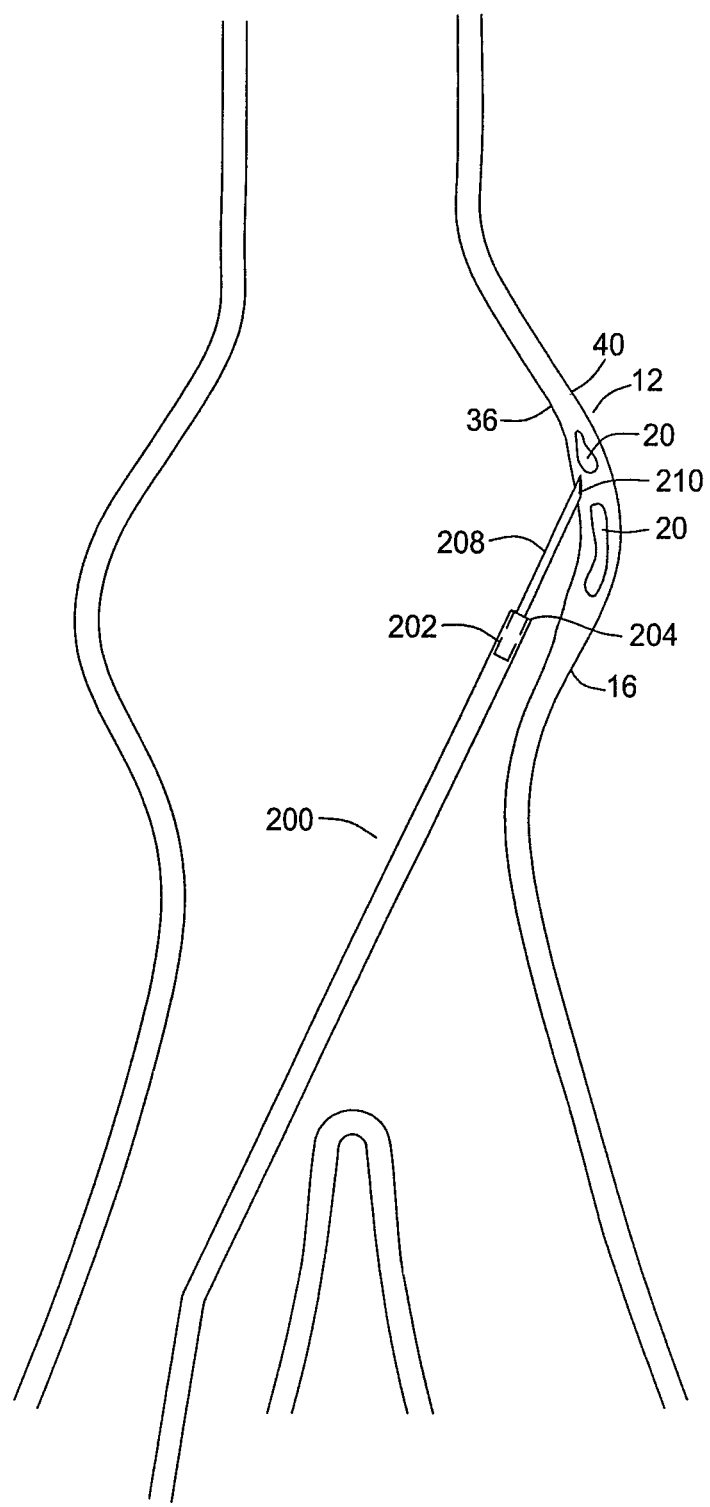
FIG. 13 is a sectional view of an aneurysmal aorta having a catheter and needle inserted therein for delivery of an intervention device within the aorta wall.

Alternatively, the carrier 20 may be positioned in the blood vessel, or the region between the Tunica Intima 36 and Tunica Media 40 intraveneously. Referring to FIG. 13, there is shown a catheter 200, which is configured to have a syringe portion 202 (shown in phantom) at the distal end 204 thereof, such that the needle 208 of the syringe portion 202 may be retracted within catheter 200 during introduction of the catheter 200 up an artery of a patient, but the needle 206 thereof may be extended, once the distal end 204 of catheter 200 is positioned within the stent graft 80 at the aneurysmal site 16. Additionally, catheter 200 includes an extension mechanism, such that the syringe may be actuated, typically by depressing the plunger thereof when the needle is properly positioned for placement of the carrier 20. Extending of the needle, and depressing of the plunger, are easily accomplished by extending wires (not shown) within the sheath of catheter 200, and linearly moving the wires while holding the sheath portion of the catheter stationary. Once the distal end 204 of catheter 200 is located adjacent to the aorta or blood vessel aneurysmal site 16, the needle 208 is extended therefrom, and inserted through into the region between the Tunica Intima 36 and Tunica Media 40 such that carrier 20 in viscous sol gel or other needle dispensable form, is dispensed through needle 208 and apertures 210. After a desired quantity of carrier 20, as determined by the practitioner or physician, is injected into the blood vessel wall, the needle 208 is withdrawn into the catheter 200, and the catheter 200 is withdrawn from the artery and the incision into the artery is closed, such as by suturing.

Solid Carriers and their Placement

Figure 4:
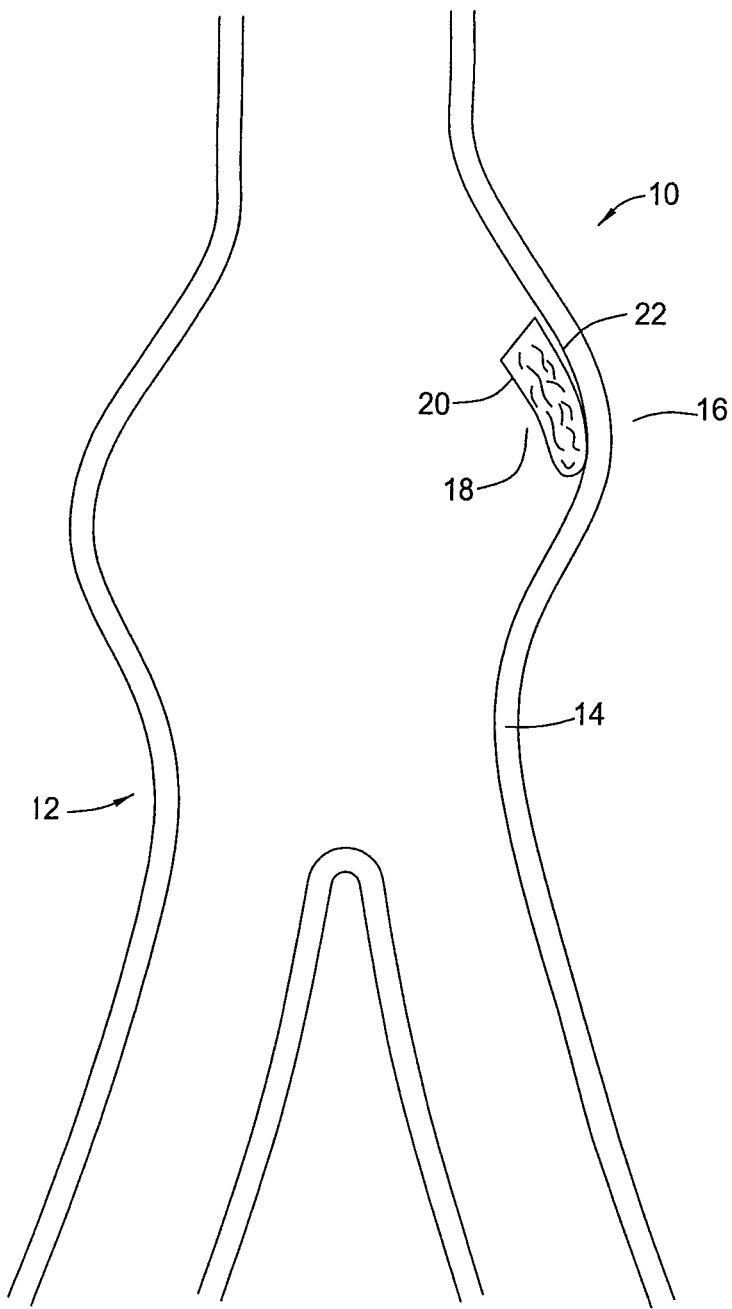
FIG. 4 is a sectional view of the aorta shown in FIG. 1, showing an additional intervention device therein for therapeutic treatment of the aneurysmal site.

Referring now to FIG. 4, there is shown the aorta 12 of FIG. 1, having an intervention device, specifically a solid based carrier 20', located therein for the time-release delivery of therapeutic agents to the blood vessel wall. Therapeutic agents include, but are not limited to, agents which reduce the incidence of elastin attacking proteins, such as antibiotics, as well as anti-inflammatories and ace-inhibitors, etc. As shown in FIG. 2, the therapeutic agent carrier 20' in this embodiment is a relatively rigid sol gel produced material, which is attached to the aneurysmal site 16 with an adhesive 22, such as a biocompatible acrylic adhesive.

Preparation of carriers for sol gel preparation is well known in the art, and when prepared, with the introduction of biological therapeutic agents, will result in a matrix from which the therapeutic agent will elute from over time. A typical sol gel preparation comprises hydrolysis and condensation of an orthosilicate such as tetramethyl orthosilicate TMOS) or tetraethyl orthosilicate (TEOS). For example, TMOS may be partially hydrolyzed in an acidic medium by addition of a controlled amount of water and the therapeutic agent is introduced in a suitable buffer to facilitate gelation. The buffer pH is chosen so as to allow the final solution to be close to neutrality in order to avoid denaturation of proteins. The resulting sol gel is a glass matrix, within which the therapeutic agent is entrapped and when exposed to fluids, such as blood in an aneurysmal sac 18, will out and into the fluid over a period of time. By varying the pore size in the matrix, the speed of diffusion may be varied, by one skilled in the art, to match the duration of efficacy and rate of diffusion for treatment of an aneurysmal site 16.

To position carrier 20' at the aneurysmal site 16, carrier 20', with adhesive attached thereto, is located at the end of an introducing system, such as a wire or catheter, which is introduced by placement thereof in an artery, the femoral artery, and the catheter or wire is pushed up the artery until the end thereof, with the carrier thereon, is positioned against the wall of the blood vessel at the aneurysmal site 16, such that adhesive 22 is in direct contact with the wall 18. The adhesive may be self-curing, in a matter of seconds or minutes, such that by maintaining contact between the adhesive and wall, the adhesive 22 will cure and bond the carrier 20' to the wall. Alternatively, the adhesive could be curable by ultraviolet light, and in such case catheter will include a light source at the end thereof adjacent the location where carrier is carried, and such light source will be activated to cause curing of the adhesive in place and thus bonding of the carrier 20', in place against the blood vessel wall. Additionally, the adhesive 22 and the carrier 20' may be separately delivered to the aneurysmal site 16 by the catheter, such that the aneurysmal blood vessel wall 14 is first coated with the adhesive 22, and the carrier 20' is then positioned in contact with the adhesive. Once bonding has occurred, the carrier 20' is released from the wire or catheter, and the catheter or wire is removed from the artery. Use of wires and catheters for the placement of intravascular devices is well known to those skilled in the art. Carrier 20'' delivers the therapeutic agent to the aneurysmal site by virtue of diffusion of the therapeutic agent therefrom.

Referring now to FIG. 5, there is shown a further embodiment of the invention, wherein carrier 20'' is composed of a micro-encapsulation element, such as a plastic, resin, or the like, which has substantially rigidity and is positioned at the aneurysmal site 16 by the use of tethers 60, 62, each of which projects through the wall of the aorta 12 at the aneurysmal site 16, and terminates in a hook 64, 66, at the distal end of each of the tethers 60, 62. Each of hooks 64, 66 include thereon a barb 68 at the tether receiving end 70 thereof, and a relatively sharp point 72, such that point 72 may be used, in conjunction with a remotely operated catheter, wire or the like (not shown), to puncture the aorta wall 14 at the aneurysmal site 16. Once point 72 has punctures aorta wall 14, hook 64 (or 66) is pushed through the aorta wall, such that barb 38 engages against the outer surface of aorta wall 14, thereby securing the tether against retraction through the hole created by sharp point 72. Each tether 60, 62 is secured within or on the carrier 20'', such as by being molded therein when the carrier 20'' is made.

In the embodiments according to the invention shown and described with respect to FIGS. 4 and 5, carrier 20', 20'' is a rigid or substantially rigid, yet porous or leaching, material. One such carrier 20' or 20''' is the rigid sol gel derived material previously described herein. Additionally, carrier may be provided as PLGA, poly Lactide, poly Lactic acid, poly glycolide, PCL, Poly(Lactide-glycolide) copolymer, Poly(Lactide-glycolide-caprolactone) copolymer, Poly(Lactide-caprolactone) copolymer, Poly(glycolide-caprolactone) copolymer, other biodegradable polymers, having the therapeutic integrally formed therein, as a porous polymer, such that the therapeutic agent may dissolved or otherwise captured in the pores thereof, or, as a polymer for which the therapeutic agent has a physical or chemical affinity, such that the therapeutic agent may be held thereby for later release into the aneurysmal site. To manufacture the carrier from a copolymer such as PLGA (poly(DL-co-glycolic-acid), which is a co-polymer the solid form of PLGA are mixed with an solvent, such that they are dissolved therein, and the therapeutic agent, and a solvent therefore, are mixed with the dissolved PLGA. Tethers 60, 62 are then located to span across yet within the mixture. Alternatively, the tethers 60, 62 may extend from a mesh which is disposed in and becomes encased in the carrier matrix when the copolymer solidifies, such that the mesh helps encapsulate the carrier 20 when used at the aneurysmal site 16. The mixture is then heated (or subjected to vacuum), to drive off the solvents, leaving behind a solid form of PLGA having the therapeutic agent held and dispersed therein. When placed in a fluid, such as blood, the PLGA will break down, releasing the therapeutic agent as it disintegrates or the agent can diffuse slowly out of the carrier.

Where a porous polymer is used as the carrier, the carrier is prepared by placing the porous polymer in a bath of the therapeutic dissolved in a solvent therefore, such as water. After a sufficient period of time for diffusion of the therapeutic agent into the carrier, the carrier is removed from the agent-solvent bath, and is ready for use. Alternatively, the polymer can be mixed with the therapeutic agent before the formation of porous structure. As a result, the therapeutic agent is distributed evenly in the matrix. Finally, where the carrier is configured from a material having a physical or chemical bonding attraction to the therapeutic agent, the carrier is likewise located in a liquid form of the therapeutic agent, such as the agent dissolved in a solvent, or the therapeutic agent is physically forced into the carrier material, such as by rolling the carrier material in a solid form of the therapeutic agent.

Figure 6:
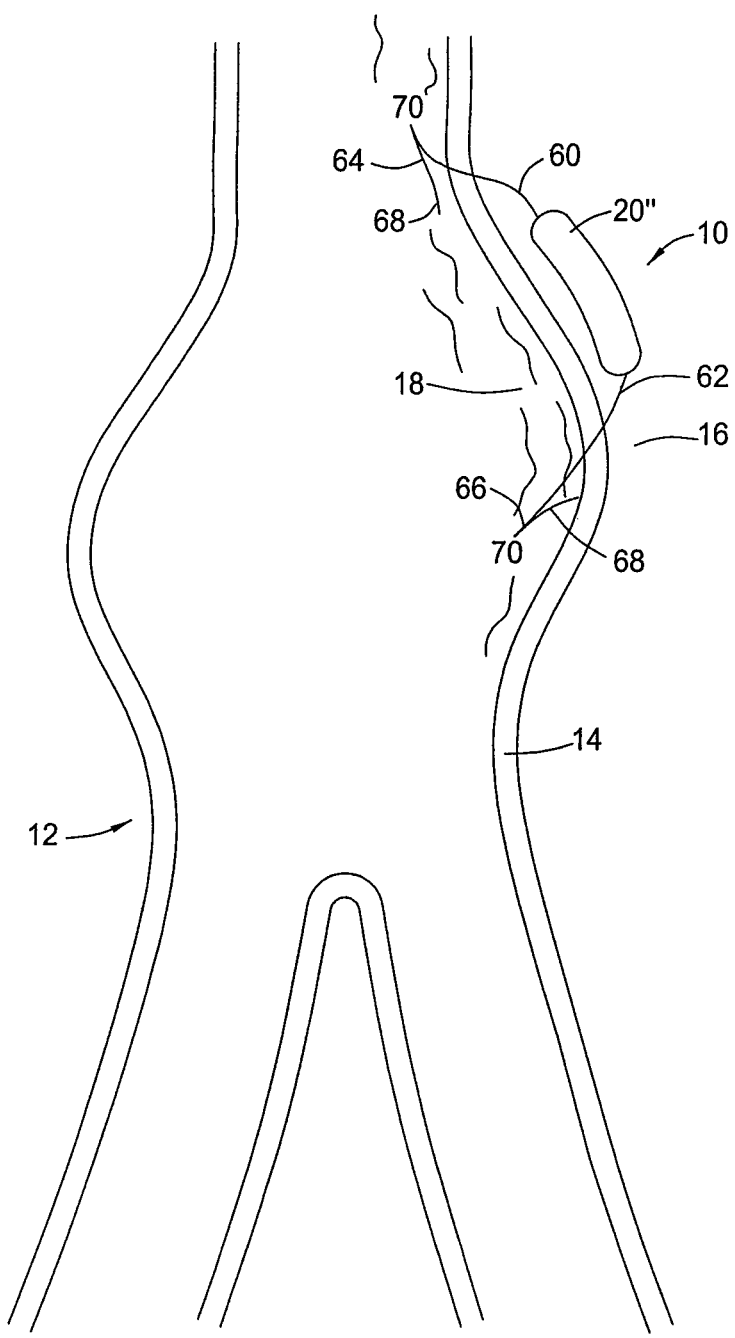
FIG. 6 is a sectional view of the aorta shown in FIG. 1, showing the intervention device of FIG. 5 located exterior of the aorta.

Referring now to FIG. 6, still a further embodiment according to the invention is shown. In this embodiment, a carrier, e.g., carrier 20''' is again provided, with the tethers 60, 62 (which are optional) and hooks 64, 66 as shown in FIG. 3, except the carrier 20''' is located outside of the aorta 12, i.e., on the exterior of the aorta 12. This positioning is enabled by making an incision through the patient's dermis, and directing a laparoscope or other such tool through the muscle and intervening tissue to the aorta site, and positioning the carrier 20''' against the aorta wall 14 on the exterior thereof, while also inserting the hooks 64, 66 into the aorta such that the barb 68 portions thereof are positioned in the aorta 12 so as to prevent carrier from pulling away therefrom. This positions the carrier 20''' against the aorta wall 14, to enable the therapeutic agent therein to ewe elute, escape or diffuse therefrom and into the aorta wall 14 for therapeutic treatment thereof. Again, in this embodiment, carrier may be any of the rigid carrier compositions described herein. Alternatively, the carrier 20''' may be positioned exterior to the aorta 12 without tethers, and maintained in place as the location has limited fluid flow therepast.

Each of the embodiments according to the invention shown and described with reference to FIGS. 1 to 6 provide time release delivery of the therapeutic agent directly to the aneurysmal site 16, without the need for systemic application of the therapeutic agent and the attendant risk of side effects therefrom. Further, each of the embodiments of the carrier 20, 20', 20'' or 20''' specifically enable timed release of the therapeutic agent, and their structure and positioning enables them to be replaced periodically, if considered necessary and prudent, through the removal thereof from the aneurysmal site by a catheter extended through the aorta 12, or by a laparoscope extended thereto through the body and the reintroduction of a new carrier 20, 20', 20'' or 20''' having fresh therapeutic agent therein, to the aneurysmal site 16.

Although the placement of a sol gel derived solid matrix carrier, e.g. 20' is described herein as being performed with an adhesive, this type of carrier is likewise readily affixed to the blood vessel wall 14 adjacent the aneurysmal site 16 with the tethers 60, 62 and hooks 64, 66 as described herein with respect to FIGS. 4 to 6. Likewise, the embodiments of the carrier described herein with respect to FIGS. 4 to 6 may also be affixed to the blood vessel wall 14 adjacent to the aneurysmal site 16 by the adhesive 22.

Although the invention has been described herein as applicable to situations wherein the carrier is placed in the aneurysmal site 16, without application of an excluding device, the use of the carrier is equally applicable to situations where an excluding device is used to internally by-pass the aneurysmal site 16 through the blood vessel itself.

Use of the Carrier in Conjunction with an Excluding Device

Figure 7:
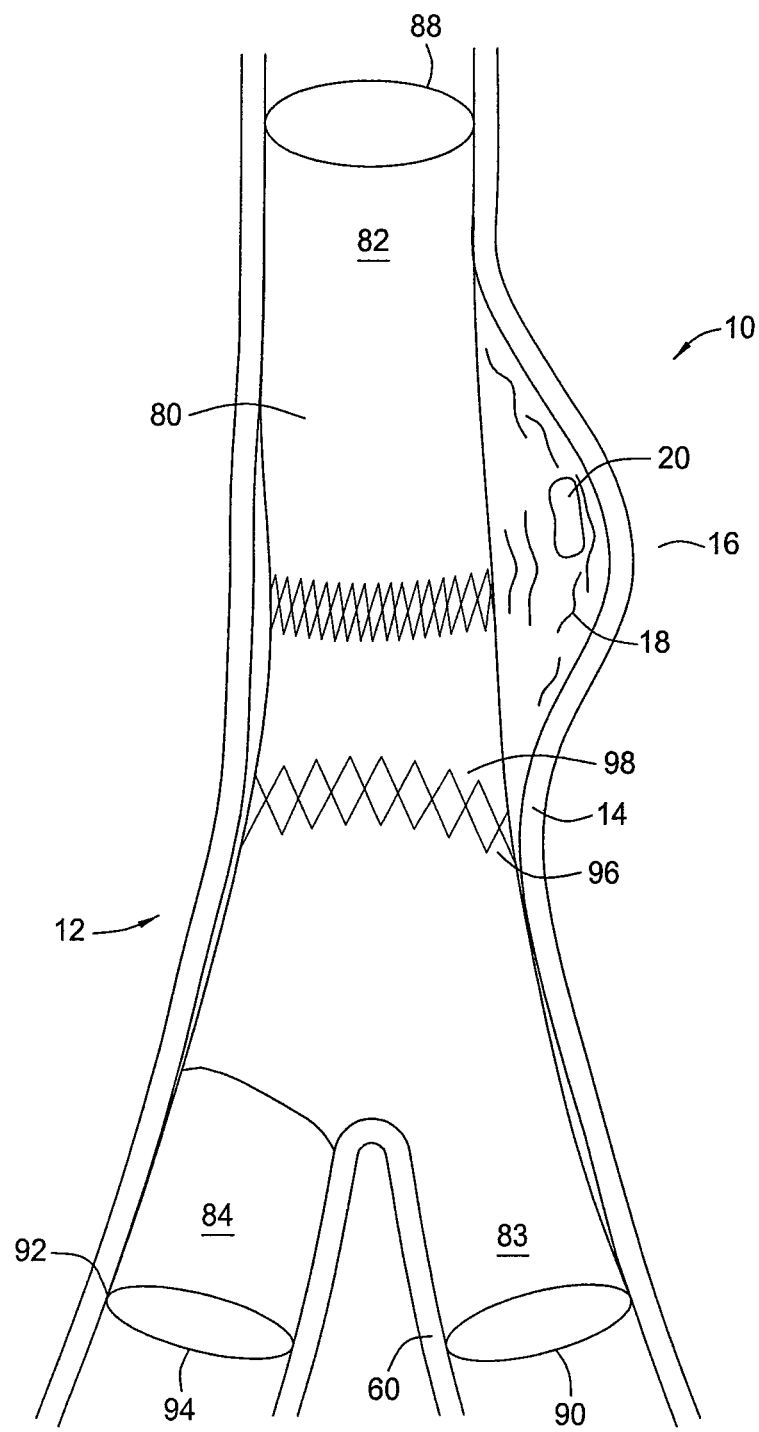
FIG. 7 is a view of the aneurysmal blood vessel of FIG. 1 showing an excluding device therein.
Figure 8:
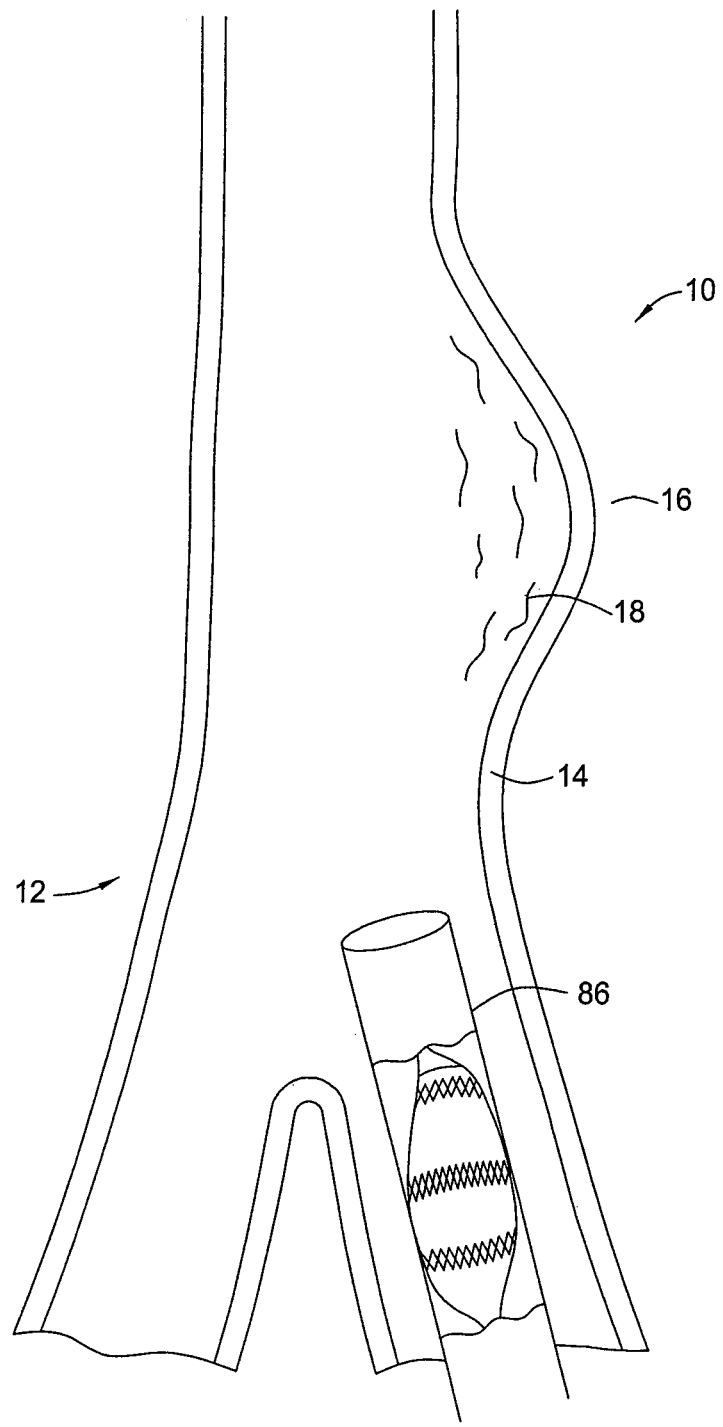
FIG. 8 is a schematic view of a placement device and location thereof for placing the excluding device of FIG. 7 in the aneurysmal blood vessel.

Referring now to FIG. 7, the aneurysmal site of the aorta 12 of FIG. 1 is shown having a stent graft 80 placed therein to span the aneurysmal site 16. In this embodiment, stent graft 80 is a modular stent graft, having a main body portion 82 having an ipsilateral extension 83 thereon, and a contralateral limb portion 84 which is separately introduced and placed in the aorta 12 from main body portion 82. To locate the stent graft 80 in the aorta 12, a sheath 86 as shown in FIG. 8, having the main body portion 82 of the stent graft 80 therein, is first inserted into the femoral artery and then pushed up the artery until the sheath extends past the aneurysmal site 16. The sheath is then removed, while the stent graft main body portion is deployed therefrom, such that the proximal end 88 of the main body portion 82 is positioned above (or beyond) the aneurysmal site 16, and the distal end 90 of the ipsilateral extension 8 is positioned below the aneurysmal site 16 within the artery 60 as shown in FIG. 7. The contra lateral limb portion 84 of the stent graft 80 is then deployed through the artery 92, on a wire, sheath 86 or the like, such that the contralateral limb portion 84 is located inside a portion of the main body portion 82 and extends therefrom down the artery 92 to its distal end 94 as also shown in FIG. 7 (only a portion of which is shown).

Referring still to FIG. 7, stent graft 80 includes both a stent portion 96, which reinforcingly engages with graft portion 98. Stent portion 96 is configured as a plurality of hoops or rings, which may be compressed for placement in the aorta 12, and once properly in position, actuated to expand and thereby press against or into the adjacent blood vessel wall 14. Thus, an actuation means, such as a sheath or manipulating wires, or the like (not shown), which when manipulated cause the generally cylindrical profile of the stent portion 96 to expand, and press against the aorta wall 14 at least at the proximal end and distal ends thereof, thereby sealing off the aneurysmal site from blood flow. Graft portion is a flexible element having sufficient strength to allow blood to pass therethrough without rupture. Typical materials for graft portion 98 include biocompatible plastics such as implantable quality woven polyester. Such polyester material may also include, therewith, components such as collagen, albumin, of an absorbable polymer or of a biocompatible fiber.

Referring again to FIG. 7, the aneurysmal sac 18 is isolated from the interior of aorta 12 by the positioning of stent graft 80, and there is positioned therein carrier 20, 20' or 20". Carrier 20, 20' or 20" may be configured of any of the structural embodiments discussed herein with respect to FIGS. 2 through 6.

Figure 9:
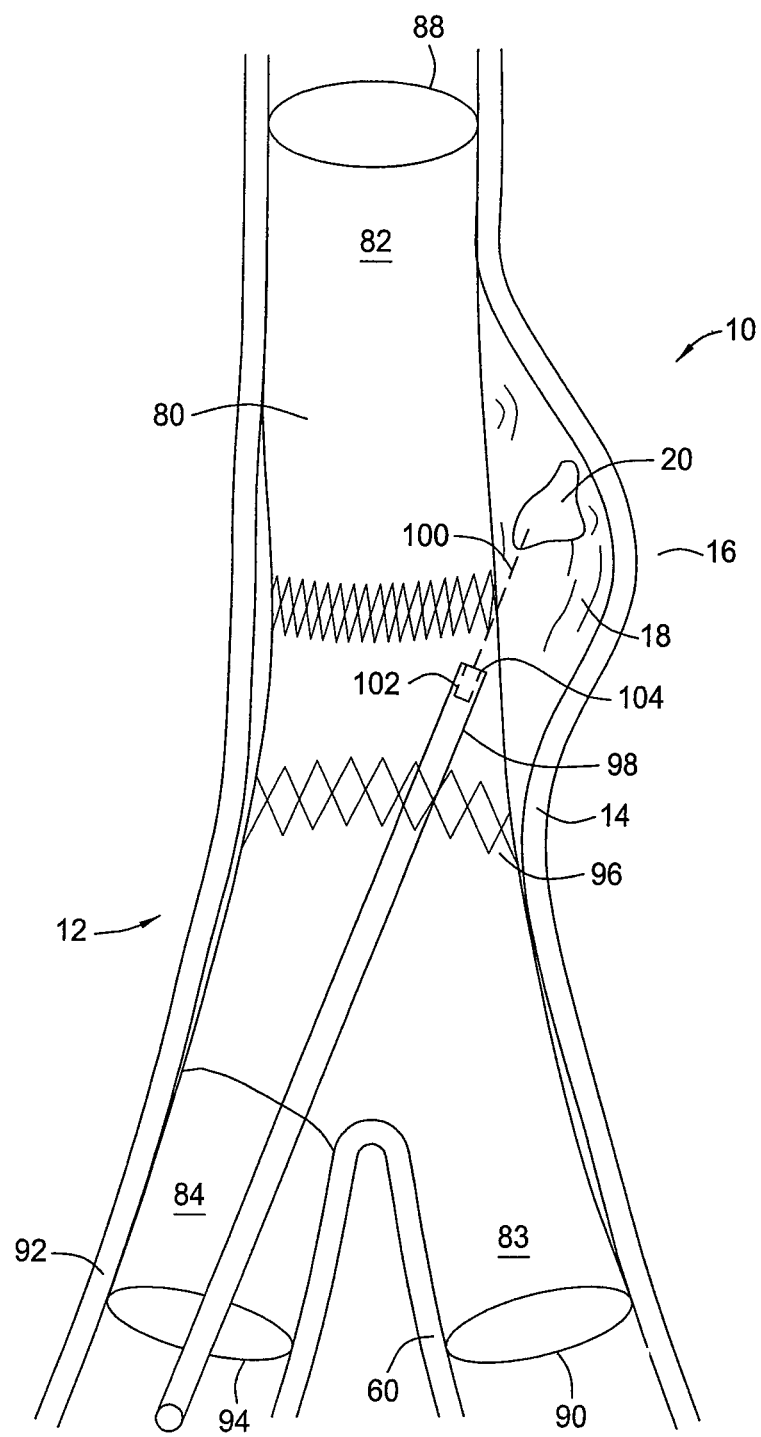
FIG. 9 is a schematic view of a placement device for locating an intervention device at the aneurysmal site after placement of the excluding device of FIG. 7 at the aneurysmal blood vessel site.

Liquid and Viscous Carrier Applications with Exclusion Device

Where a carrier 20"" is configured as a viscous sol gel carrier, the carrier may be readily introduced to the aneurysmal site 16 after placement of the stent graft 80, by injecting the carrier through a needle extending from the artery, i.e., blood flow side of the stent graft 80 to the aneurysmal sac 18 side thereof. To provide the placement of the carrier 20"", a catheter 100 as shown in FIG. 9 is configured to have a syringe portion 102 (shown in phantom) at the distal end 104 thereof, such that the needle 108 of the syringe portion 102 may be retracted within catheter 100 during introduction of the catheter up an artery of a patient, but the needle 106 thereof may be extended, once the distal end 104 of catheter 100 is positioned within the stent graft 80 at the aneurysmal site 16. Additionally, catheter 100 includes an extension mechanism, such that the syringe may be actuated, typically by depressing the plunger thereof when the needle is properly positioned for placement of the carrier 20"". Extending of the needle, and depressing of the plunger, are easily accomplished by extending wires (not shown) within the sheath of catheter, and linearly moving the wires while holding the sheath portion of the catheter stationary. Once the distal end 104 of catheter 100 is located in stent graft 80, needle 108 is extended therefrom, and inserted through the graft portion of stent graft 80 such that one or more apertures (not shown) in needle 108 are exposed to aneurysmal sac 18, and carrier 20"", in viscous sol gel or other needle dispensable form, is dispensed through needle 108 and apertures 110 into aneurysmal sac 16. After a desired quantity of the carrier 20"" as determined by the practitioner or physician, is injected into the aneurysmal sac 18, the needle 108 is withdrawn into the catheter 100, and the catheter 100 is withdrawn from the patient and the incision into the artery and the dermis is closed, such as by suturing.

Alternatively, it is also contemplated herein that the liquid or gel based carrier may be introduced into the aneurysmal sac 18 by external means, such as by directing a laparoscope having a syringe thereon, through the dermis and to a position adjacent to, and exterior of, the aneurysmal sac 18, and extending a needle on the syringe through the aorta wall 14 to a position within aneurysmal sac 18. Thence the gel or liquid carrier is introduced through the needle, and the needle is withdrawn. This methodology may also be used to dispense microsphere carriers, such as those manufactured from a copolymer such as PLGA, so long as the microsphere diameter is less than that of the needle aperture. Thus carrier 20"", with the capability for time release of therapeutic agents therein, may be externally positioned in the aneurysmal sac 18 and maintained therein by the excluding character of stent graft 80. Alternately, the carrier/drug can be delivered inside the vessel wall, outside the aneurysm sac or in the adventitial layer of the vessel wall.

Figure 10:
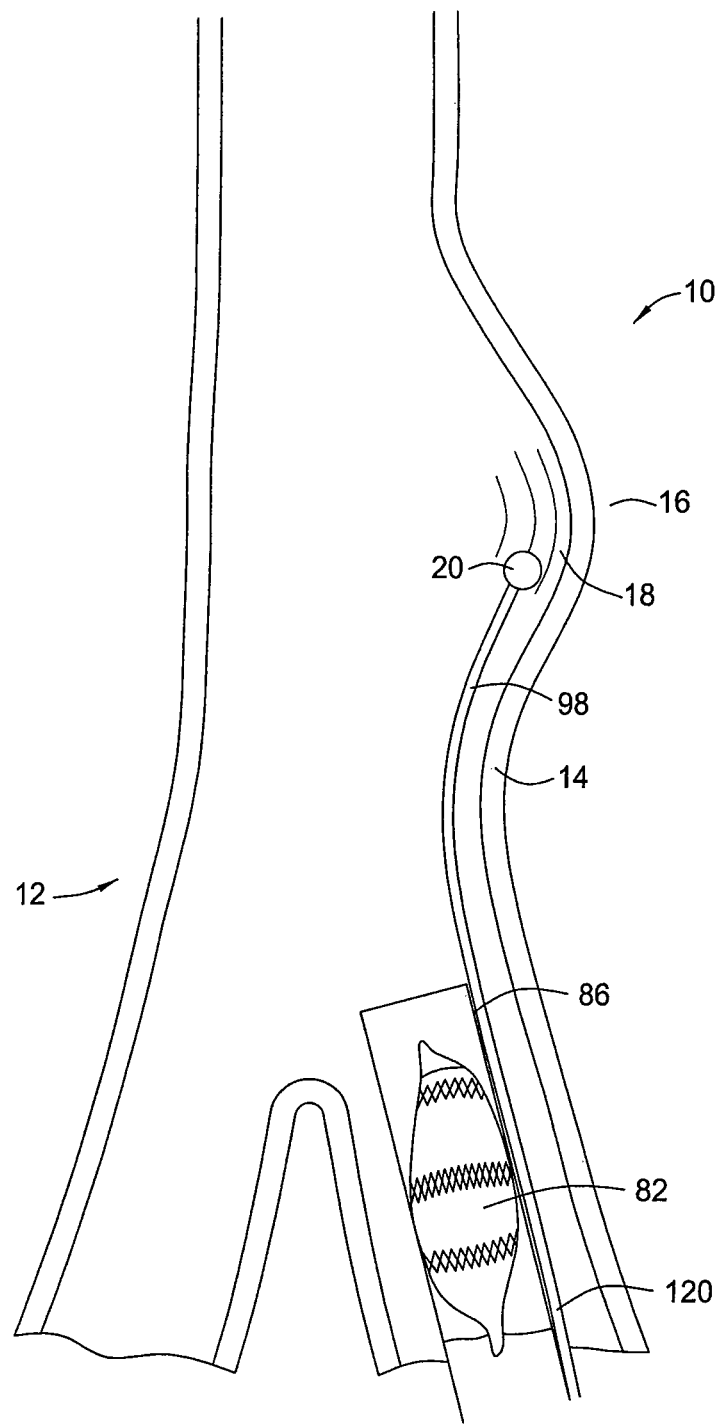
FIG. 10 is a schematic view of an alternative placement device for locating an intervention device at the aneurysmal site after placement of the excluding device of FIG. 7 at the aneurysmal blood vessel site.
Figure 11:
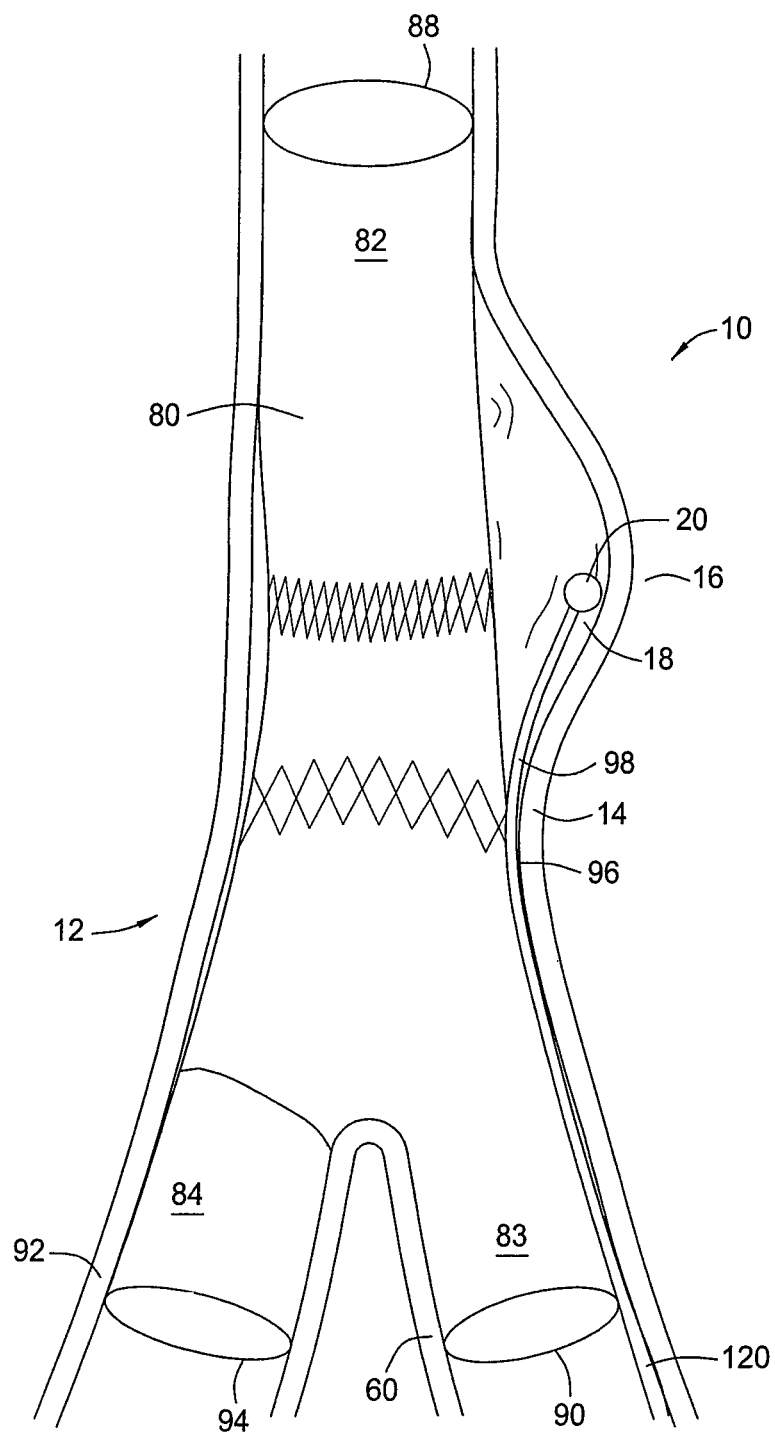
FIG. 11 is a schematic view of an alternative placement regimen for locating an intervention device at the aneurysmal site after placement of the excluding device of FIG. 7 at the aneurysmal blood vessel site.
Figure 12:
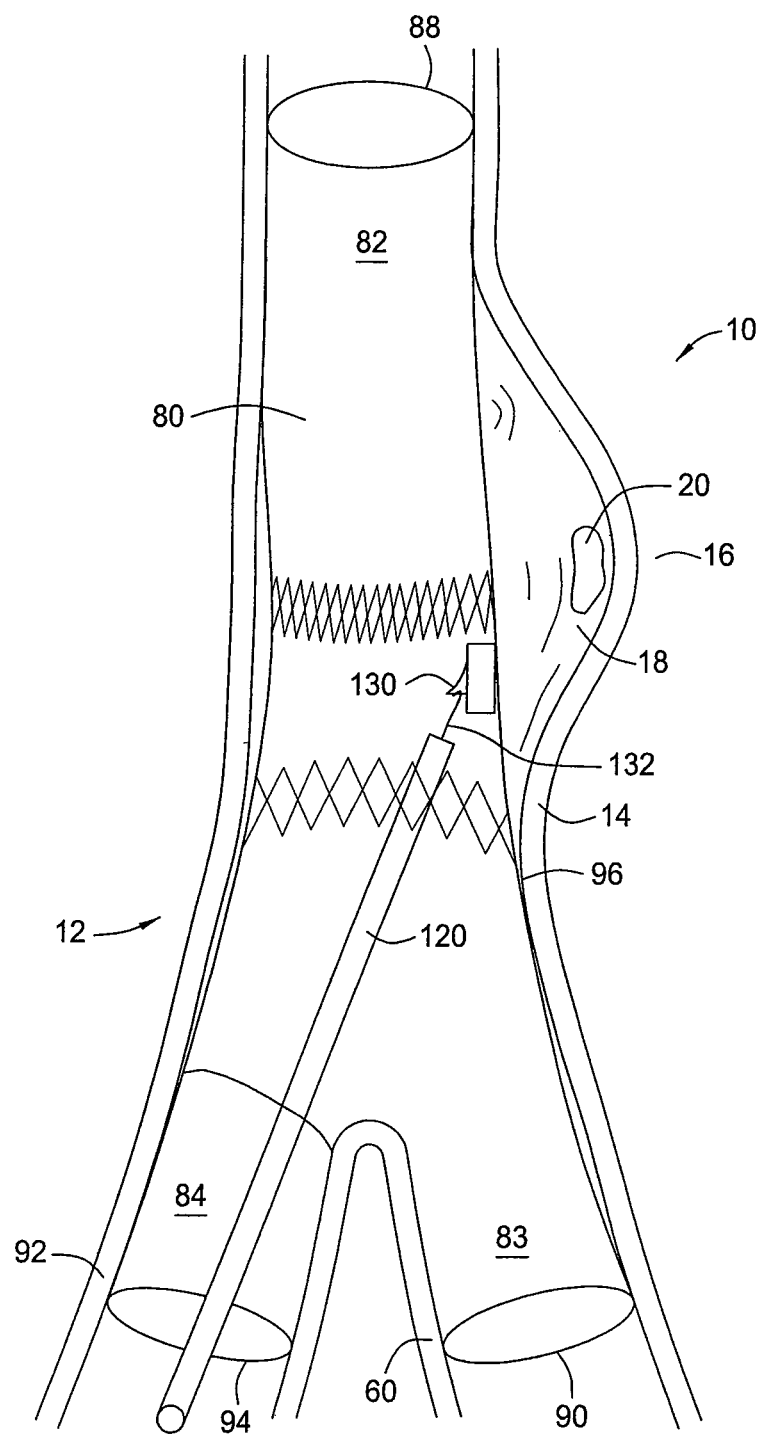
FIG. 12 is a sectional view of an aneurysmal blood vessel having an alternative structure of an excluding device therein.

Although a carrier such as sol gel is readily introducible to the aneurysmal sac 18 after the placement of an excluding device such as stent graft 80, carriers having solid form which is larger than can readily pass through the needle can also be used in conjunction with an excluding device, but alternate placement is necessary. Referring first to FIGS. 10 to 12, there is shown a first mechanism for placing solid carriers, such as PLGA, plastic, resin or other base carriers (e.g. 20) into aneurysmal sac 18 where an exclusion device is placed to span the aneurysmal site 16. As shown in FIG. 10, a carrier e.g. 20 is positioned within the aneurysmal region of aorta 12, at the aneurysmal sac 18, by virtue of catheter 120 which has been inserted into a leg artery such that carrier e.g. 20 was pushed up the artery to aneurysmal sac 18 before the stent graft 80 is deployed. Then, as shown in FIG. 11, a stent graft 80 is positioned within aorta 12 to span the aneurysmal site 16, while catheter 120 maintains the carrier e.g. 20 in position in aneurysmal sac 18. The placement of stent graft 80 in aorta 12 is well know in the art, and has been generally set forth previously herein. Once the stent graft 80 is properly positioned in aorta 12, carrier e.g. 20 is released from the catheter 120, and catheter is 120 is removed from aorta 12 and the leg artery, and the incisions are closed. Thus, a carrier e.g. 20 having a size or consistency which prevents placement into an aneurysmal sac 18 through a needle may be readily placed with catheter 120 maintained in place during stent graft 80 deployment. Further, this methodology of deployment may also be used with flowable sol gel or liquid agents, by maintaining them in a dispensing apparatus in end of the catheter 120 maintained in the aneurysmal sac 18 during stent graft 80 deployment, and dispensing them into the then isolated aneurysmal sac 18 region before removing catheter 120. In each instance, whether carrier e.g. 20 is in liquid, solid or gel form, the carrier will remain within aneurysmal sac 18, or trapped between the stent graft 80 and the adjacent contacted regions of aorta wall 14, as stent graft 80 isolates aneurysmal sac 18 from the remainder of aorta 12. Thus, the carrier e.g. 20 need not be otherwise attached to the aneurysmal location. Additionally, after the efficacy of carrier e.g. 20 is extinguished, such as when the level of therapeutic agent eluted or dispensed therefrom reaches a threshold minimum value, the carrier e.g. 20 can be replaced by again introducing catheter 120 into aorta 12, manipulating it into the isolated aneurysmal sac 18, and placing a new carrier e.g. 20 therein. Where carrier e.g. 20 is one which degrades over time, such as PLGA, certain sol gel type or other soluble type carriers e.g. 20 the new or replacement carrier e.g. 20 may be positioned in aneurysmal sac 18 without the need to remove the earlier placed carrier e.g. 20. Where the carrier e.g. 20 is non degradable, such as a plastic carrier, the earlier carrier e.g. 20 typically should first be retrieved by the catheter 120, before a replacement carrier e.g. 20 is placed therein.

The carrier may also be placed into the aneurysmal sac 18 isolated behind stent graft 80 by virtue of providing an alternative structure in the stent graft 80, such that a door 130 is provided in stent graft 80 to provide access between the interior of the blood vessel and the aneurysmal sac 18. Referring now to FIG. 12, stent graft 80 is shown having a door 130 extending through the graft portion thereof, such that door 130 may be manipulated, by a hook 132 or other device on the end of a wire or catheter 120, between an open position (shown in FIG. 12) and a closed position (not shown). To place carrier e.g. 20 into the isolated aneurysmal sac 18, door 130 is opened, such as by a locating a hook 132 adjacent thereto by introducing the hook on the end of a wire or of catheter 120, and using such hook to manipulate the door 120 open. The hook is then withdrawn into its own sheath in the end of catheter 120, or moved upwardly in aorta 12 to a non-interfering position with respect to door 130, and then an additional wire (not shown) is directed from catheter 120, holding carrier 20" thereon or therein, into aneurysmal sac 18. Carrier 20" is then released from catheter 120 to be deposited in the aneurysmal sac 18, and the wire is withdrawn through door 130. Catheter 120 is then manipulated, in conjunction with hook 132, to position hook 132 to close door 130. Catheter 120 is then withdrawn from the body, and the incisions through which they were placed are closed.

Carrier e.g. 20 so placed may be any of the carrier configurations discussed herein, and when placed in aneurysmal sac 18, is isolated from the blood flowing through aorta 12 and therefore will remain in place in aneurysmal sac 18 to release the therapeutic agents therein into any fluids in the aneurysmal sac 18, and where in direct contact with wall 14, directly thereto. Additionally, the presence of door 130 enables replacement of carrier e.g. 20 with an additional carrier e.g. 20 after the efficacy of the previously placed carrier becomes limited. Furthermore, the use of the door enables placement of solid carriers e.g. 20' into the aneurysmal sac 18 isolated by the stent graft 80, as well as liquid or gel carriers e.g. 20. Such liquid or gel based carriers may be dispensed into the aneurysmal sac 18 through a syringe or other dispensing media held in catheter 120 when the end thereof is extended into aneurysmal sac 18 through door 130. Alternatively, the opening on the graft for the catheter to pass through can be covered by a cuff which can be placed on top of the opening after the carrier is delivered.

Although the invention herein has been described in terms of multiple individual embodiments, it should be understood that various of the embodiments hereof may be combined for effective aneurysm treatment. For example, an aneurysm may first be treated by positioning a carrier e.g. 20 in the aneurysmal site 16 without the presence of an excluding device, as described herein such as by the use of an intravascular catheter, a laparoscope, or the like. This may be done repeatedly over a period of time, replacing used carriers e.g. 20 with fresh carriers e.g. 20, and if the aneurysm does not progress, no further intervention may be necessary. Additionally, different carrier and delivery regimes may be undertaken at the same aneurysmal site 18, such that a sol-gel based carrier e.g. 20 is first adhered to the interior or exterior of the aneurysmal aorta wall 14, and once the efficacy thereof is diminished, a different regime, such as introduction of sol gel or liquid carrier within the blood vessel itself, or a solid carrier e.g. 20 tethered to the blood vessel wall 14 at the aneurysmal site 16 may then be used. Further, an excluding device such as stent graft 80 may be introduced initially, before therapeutic agent treatment of the aneurysmal site 16 is initiated, such that carrier e.g. 20 may be placed therewith, or introduced therewith or in the same procedure, or, carrier e.g. 20 may be introduced later introduced such as through intravenous or laparoscopic introduction. Therefore, the invention provides multiple solutions to aneurysm treatment, with minimal invasiveness to the patient and with the capacity to modify the treatment plan in response to patient reaction to the treatment.

We claim:

1. An apparatus for the placement of time released therapeutic agents in an aneurysmal blood vessel wall location, wherein the blood vessel includes an interior surface and an exterior surface; comprising:
   a solid carrier having the therapeutic agent therein and a mechanism for the time release of the therapeutic agent therefrom, wherein the carrier comprises a sol-gel or a degradable matrix and further comprises a tether; and
   an adhesive extending between said carrier and the blood vessel wall adjacent the aneurysmal location for positioning the carrier in proximity to the aneurysmal location of the blood vessel.

2. The apparatus of claim 1, wherein said apparatus further includes an exclusion device spanning the aneurysmal blood vessel wall location.

3. The apparatus of claim 1, wherein said carrier further includes microspheres.

4. The apparatus of claim 1, wherein said carrier is degradable, over time, to release therapeutic agent therefrom.

5. The apparatus of claim 1, wherein said carrier is introduced to said aneurysmal blood vessel wall location through said exclusion device.

6. The apparatus of claim 2, wherein said exclusion device includes a door therein.

7. The apparatus of claim 1, wherein said carrier is not a stent.

8. An apparatus for treatment of aneurysmal sites in blood vessels, comprising:
   a solid carrier having a therapeutic agent therewith and releasable, over a period of time, therefrom, wherein the carrier comprises a sol-gel or a degradable matrix and further comprises a tether; and
   an introduction device for placing said carrier and an adhesive in said location within the blood vessel.

9. The apparatus of claim 8, wherein said introduction device is a catheter disposable through a blood vessel and directable to the aneurysmal location.

10. The apparatus of claim 8, wherein said introduction device includes a needle, and said adhesive contacts the media Tunica Adventitia and Tunica Intima adjacent the aneurysmal site.

11. The apparatus of claim 8, wherein said carrier further includes microspheres.

12. The apparatus of claim 8, wherein said apparatus further includes an excluding device disposed with the blood vessel and spanning the blood vessel site.

13. The apparatus of claim 12, wherein said excluding device includes a membrane therewith or a door therethrough.

14. The apparatus of claim 1, wherein the tether further comprises a hook, a barb, or a combination thereof.

15. The apparatus of claim 8, wherein the tether further comprises a hook, a barb, or a combination thereof.

* * * * *